(12) United States Patent
Janssen et al.

(10) Patent No.: US 8,545,576 B2
(45) Date of Patent: Oct. 1, 2013

(54) PROCESS FOR PRODUCING A COLORANT FOR KERATIN FIBERS

(71) Applicant: Henkel AG & Co. KGaA, Duesseldorf (DE)

(72) Inventors: Frank Janssen, Neuss (DE); Juergen Schoepgens, Schwalmtal (DE)

(73) Assignee: Henkel AG & Co., KGaA, Duesseldorf (DE)

( * ) Notice: Subject to any disclaimer, the term of this patent is extended or adjusted under 35 U.S.C. 154(b) by 0 days.

(21) Appl. No.: 13/782,525

(22) Filed: Mar. 1, 2013

(65) Prior Publication Data

US 2013/0174356 A1    Jul. 11, 2013

Related U.S. Application Data

(63) Continuation of application No. PCT/EP2011/058793, filed on May 30, 2011.

(30) Foreign Application Priority Data

Oct. 20, 2010 (DE) .......................... 10 2010 042 659

(51) Int. Cl.
*A61Q 5/10* (2006.01)

(52) U.S. Cl.
USPC ............... 8/405; 8/406; 8/435; 8/475; 8/500; 8/501; 8/580

(58) Field of Classification Search
USPC ............. 8/405, 406, 435, 475, 500, 501, 521, 8/580

See application file for complete search history.

(56) References Cited

U.S. PATENT DOCUMENTS

| 3,548,562 A | 12/1970 | Schwartzman |
| 4,635,822 A | 1/1987 | Klawitter |
| 5,061,289 A | 10/1991 | Clausen et al. |
| 2006/0002965 A1 * | 1/2006 | Hoeffkes et al. ............... 424/401 |

FOREIGN PATENT DOCUMENTS

| DE | 3625916 A1 | 2/1988 |
| DE | 19905768 A1 | 8/2000 |
| EP | 0132511 A2 | 2/1985 |
| EP | 2062616 A1 | 5/2009 |
| GB | 1125528 A1 | 8/1968 |
| WO | 2005067874 A1 | 7/2005 |

OTHER PUBLICATIONS

European Patent Office, International Searching Authority, International Search Report mailed Jan. 5, 2012; International Appln. No. PCT/EP2011/058793, filed May 30, 2011.

* cited by examiner

*Primary Examiner* — Eisa Elhilo
(74) *Attorney, Agent, or Firm* — Krista A. Kostiew

(57) ABSTRACT

A method for manufacturing a coloring agent for keratin fibers is provided. The method includes directing a composition A from a container A by a filler apparatus through an inlet opening into a container B containing a composition B. The coloring agent for keratin fibers exits from the container B as a mixture of the composition A and the composition B. The composition B contains a fatty alcohol, an alkoxylated fatty alcohol, and a fatty acid.

20 Claims, No Drawings

PROCESS FOR PRODUCING A COLORANT FOR KERATIN FIBERS

CROSS-REFERENCE TO RELATED APPLICATION

This is a continuation of International Application No. PCT/EP2011/058793, filed May 30, 2011, which was published under PCT Article 21(2) and which claims priority to German Application No. 102010042659.8, filed Oct. 20, 2010, which are all hereby incorporated in their entirety by reference.

TECHNICAL FIELD

The technical field relates generally to a process for producing products for keratin fibers, and more particularly relates to a process for producing a colorant for keratin fibers.

BACKGROUND

Human hair is treated nowadays with cosmetic hair preparations in many ways. These include, for example, cleaning the hair with shampoos, care and regeneration using rinses and therapies, and bleaching, coloring, and reshaping the hair using coloring agents, toning agents, waving agents, and styling preparations. Agents for modifying or tinting the color of head hair play a predominant role in this context.

For temporary coloring, it usual to use coloring or toning agents that contain so-called substantive dyes as a coloring component. These are dye molecules that absorb directly onto the substrate and do not require an oxidizing process in order to form the color. Included among these dyes are, for example, henna, which has been known since antiquity for coloring the body and hair. These color results are, as a result, much more sensitive to shampooing than are the oxidation-based colors, so that a (very often undesirable) shift in tint, or even a visible loss of color, then occurs much more quickly.

So-called oxidizing coloring agents are used for permanent, intense coloring results with corresponding fastness properties. Such coloring agents usually contain oxidation dye precursors, so-called developer components and coupler components. The developer components, under the influence of oxidizing agents or atmospheric oxygen, form among one another, or by coupling with one or more coupler components, the actual dyes. The oxidizing coloring agents are notable for outstanding, long-lasting color results. For natural-looking coloring results, it is usually necessary to use a mixture of a larger number of oxidation dye precursors; in many cases, substantive dyes are also used for toning.

These coloring agents, in particular oxidizing coloring agents or hair-bleaching powders, are as a rule manufactured by manually mixing prefabricated active-substance compositions, for example two oxidizing coloring agents or two bleaching agents. Manual intermixing is, however, time- and labor-intensive; for example, the constituents need to be weighed out before mixing. In addition, homogenization of the mixture by manual mixing of the active substances is time-intensive. The user is furthermore exposed to dust that may occur when processing solid active-substance compositions.

In light of this, US patent application 2005/0169871 A1 (L'Oreal) describes a method for manufacturing active-substance mixtures for hair treatment, in which method a liquid is directed, at elevated temperature and at a pressure above 3 bar, through a polymer-containing preparation. Although this method is suitable for manufacturing a mixture of the active substances being used, the mixture obtained nevertheless, because of its inhomogeneity and insufficient viscosity, leaves room for improvement especially for utilization in hair coloring.

Accordingly, it is desirable to provide an improved process for producing a colorant for keratin fibers. In addition, other objects, desirable features and characteristics will become apparent from the subsequent summary and detailed description, and the appended claims, taken in conjunction with the accompanying drawings and this background.

SUMMARY

A method for manufacturing a coloring agent for keratin fibers is provided. The method includes directing a composition A from a container A by a filler apparatus through an inlet opening into a container B containing a composition B. The coloring agent for keratin fibers exits from the container B as a mixture of the composition A and the composition B. The composition B contains a fatty alcohol, an alkoxylated fatty alcohol, and a fatty acid.

DETAILED DESCRIPTION

It has now been found that the aforementioned disadvantages of conventional mixing methods can be eliminated by a method for manufacturing a coloring agent for keratin fibers, in accordance with an exemplary embodiment, from a composition A and a composition B, in which method:

the composition A is directed from a container A
by a filler apparatus
through an inlet opening
into a container B containing the composition B, and the coloring agent for keratin fibers exits from the container B as a mixture of compositions A and B,
wherein the composition B encompasses
a) a fatty alcohol, as well as
b) an alkoxylated fatty alcohol, and
c) a fatty acid.

In the context of the method according to an embodiment, two compositions A and B differing from one another are mixed with one another, forming a coloring agent for keratin fibers.

Composition A is introduced from a container A. This container A is configured in an embodiment as a storage container, and encompasses several times the quantity of composition A needed for carrying out a single mixing method. In other words, in an embodiment, a sub-quantity a of composition A present in container A is introduced into container B, a residual quantity of composition A present in container A remaining in container A until the end of the mixing method, and that residual quantity corresponding to twice, for example at least four times, and in particular at least eight times the quantity of sub-quantity a.

In a further embodiment, container A comprises two or more chambers (e.g.: A1 and A2) in which compositions (e.g. A1 and A2) differing from one another are present separately from one another. The apparatus used to carry out the method is embodied in such a way that the user selects between the two or more chambers or alternatively uses, for example, a composition A1 in a first mixing method and a composition A2 in the subsequent mixing method.

Alternatively to the above-described multi-chamber configuration of container A, the apparatus for carrying out the method according to an embodiment also provides two or more separate containers for the reception of different compositions A.

In an embodiment, the introduction of composition A from container A into container B is accomplished by a directing system attaching to container A. Located at the end of this directing system is the filler apparatus provided for introducing composition A into container B. To shorten the duration of the method and to improve the method's results, in particular the intermixing quality, composition A is introduced into container B for example at a pressure above about 1.1 bar, for example above about 2.0 bar, for example above about 5.0 bar, such as in the range of from about 10 to about 20 bar.

Composition A is introduced in the course of the method into container B, out of which the coloring agent for keratin fibers then exits from container B as a mixture of compositions A and B.

In an embodiment, container B used for this is fastened by an adhesive, latching, snap-on, or clamping mechanism in the apparatus used to carry out the method.

Container B, in an embodiment, is embodied in the form of a sealed capsule. This sealed capsule is opened by the directing system conveying composition A. The opening operation occurs by penetration of the container wall of container B, for example by the filler apparatus located at the end of the directing system. This filler apparatus can be embodied, for example, in the form of a spike. Once the container wall has been punched through, composition A is then introduced into container B.

In another embodiment, at least one exit opening is formed in container B as a result of the introduction of composition A. The reason for the formation of the exit opening can be, for example, the increasing pressure in container B. Alternatively, however, the exit opening can also be formed by the action of the filler apparatus, for example by the fact that the filler apparatus pushes through the container wall of container B at two points, or by the fact that the pressure occurring in the container as a result of penetration of a container wall causes formation of the exit opening.

Methods contemplated herein in which container B is formed by the introduction of composition A, and/or the action of the filler apparatus forms at least one exit opening from which the coloring agent for keratin fibers exits from container B as a mixture of compositions A and B, make possible simple and effective mixing of the compositions being used.

The formation of the exit opening in the container wall of container B, in particular the exact location at which said exit opening is formed, is controlled by the specific construction of container B, in an exemplary embodiment.

In a first embodiment, container B possesses a weakening line along which the exit opening is formed as a result of the introduction of composition A and/or the action of the filler apparatus.

In a second embodiment, the container possesses a membrane that is pressed against a spike, accompanied by formation of the exit opening, as a result of the introduction of composition A and/or the action of the filler apparatus. The membrane is a constituent of the container wall of container B. The exit opening is generated by the penetration of the membrane by the spike. The spike can be arranged both inside container B and outside container B. In the case of a spike arranged inside container B, the container wall of container B is opened from the inside outward. If the spike is located outside container B, the spike pushes the container wall from the outside inward. In an embodiment, the container wall of container B comprises, in the area of action of the spike, a weakening line by which, for example, the size of the exit opening can be influenced.

In a further embodiment, to improve the mixing effect, composition A and/or the mixture of compositions A and B passes through a static mixer in the course of the method. This static mixer can be arranged, for example, inside the above-described directing system, but is preferably located in the immediate vicinity of the exit opening of container B, for example inside container B or outside the exit opening. In the latter case the static mixer can be embodied as an integral constituent of container B. Alternatively, the static mixer is a constituent of the apparatus used to carry out the method, and is associated, for example, with the adhesive, latching, snap-on, or clamping mechanism used to fasten container B.

Particularly homogeneous mixing of the compositions being used is achieved due to the arrangement of a static mixer inside container B, and methods contemplated herein in which container B comprises a static mixing element in its interior are therefore suitably used.

Composition B present in container B is discharged in the course of the method by the introduced composition A, out of container B through the exit opening. Discharge occurs, in an embodiment, substantially completely. In other words, at least about 80 wt. %, for example at least about 90 wt. %, for example at least about 95 wt. %, such as at least about 98 wt. % of composition B is discharged from the container.

In an embodiment, the volume ratio of compositions A and B used in the mixing method is from about 10:1 to 1:1, such as about 6:1 to about 2:1. The absolute volume of composition A used is for example in the range of from about 5 to about 500 ml, for example from about 10 to about 400 ml, such as from about 20 to about 300 ml.

In another embodiment, the weight ratio of compositions A and B used in the method is in the range of from about 1:1 to about 20:1, for example from about 2:1 to about 10:1, such as from about 3:1 to about 8:1.

In an embodiment, compositions A and B are not heated by an external heat source in the course of the mixing method. The temperature of composition A may be less than about 35° C., for example less than about 30° C., such as less than about 25° C. The temperature of the coloring agent for keratin fibers upon exiting from container B likewise may be for example less than about 35° C., for example less than about 30° C., such as less than about 25° C.

In another embodiment, the coloring agent for keratin fibers that is obtained as the end product of the method has a pH in the range of from about 5 to about 12, such as from about 7.5 to about 11.

The method contemplated herein is suitable for manufacturing coloring agents for keratin fibers having a viscosity above about 20,000 mPas (Brookfield viscosimeter, spindle 5, 4 rpm), for example in the range of from about 20,000 to about 100,000 mPas (Brookfield viscosimeter, spindle 5, 4 rpm), such as from about 25,000 to about 40,000 mPas (Brookfield viscosimeter, spindle 5, 4 rpm).

In an exemplary embodiment, to adjust the viscosity of composition B and of the coloring agent for keratin fibers, and to achieve sufficient homogeneity for the coloring agent for keratin fibers, composition B contains a fatty alcohol in combination with an alkoxylated fatty alcohol and a fatty acid.

In an embodiment, the use of fatty alcohol a) from the group of $C_8$ to $C_{22}$ fatty alcohols, for example from the group of $C_{10}$ to $C_{20}$ fatty alcohols, and in particular from the group of $C_{12}$ to $C_{18}$ fatty alcohols has proven particularly suitable in terms of the viscosity and homogeneity of the coloring agent for keratin fibers that is obtained. The weight proportion of the fatty alcohol in terms of the total weight of composition B is for example from about 0.1 to about 10 wt. %, for example from about 0.15 to about 8.0 wt. %, such as from about 0.2 to about 6.0 wt. %.

Fatty alcohols a) are combined, according to an embodiment, with an alkoxylated fatty alcohol b). The use of alkoxylated fatty alcohol b) from the group of ethoxylated fatty alcohols, for example from the group of ethoxylated $C_8$ to $C_{16}$ fatty alcohols, such as from the group of ethoxylated $C_8$ to $C_{14}$ fatty alcohols has proven particularly suitable in terms of the viscosity and homogeneity of the coloring agent for keratin fibers that is obtained. The weight proportion of the alkoxylated fatty alcohol in terms of the total weight of composition B is for example from about 0.1 to about 40 wt. %, for example from about 1.0 to about 30 wt. %, such as from about 2.0 to about 20 wt. %.

The fatty alcohols a) and alkoxylated fatty alcohols b) are further combined according an embodiment with a fatty acid c). The use of fatty acid c) from the group of $C_8$ to $C_{24}$ fatty acids, for example from the group of $C_{12}$ to $C_{22}$ fatty acids, such as from the group of $C_{14}$ to $C_{20}$ fatty acids has proven particularly suitable in terms of the viscosity and homogeneity of the coloring agent for keratin fibers that is obtained. The weight proportion of the fatty acid in terms of the total weight of composition B is for example from about 1.0 to about 20 wt. %, for example from about 2.0 to about 18 wt. %, such as from about 5.0 to about 15 wt. %.

The viscosity properties of composition B with respect to the coloring agent for keratin fibers that is obtained by mixing compositions A and B, and the homogeneity properties of the mixture, can be further improved by the addition of oil components or alkoxylated fatty alcohol sulfates.

Accordingly, in an embodiment, composition B contains an oil component having a melting point below about 25° C. from the group of the paraffins. The weight proportion of the oil component in terms of the total weight of composition B is for example from about 0.1 to about 50 wt. %, for example from about 1.0 to about 40 wt. %, such as from about 5.0 to about 30 wt. %.

In another embodiment, composition A and/or composition B contains an alkoxylated fatty alcohol sulfate, for example an ethoxylated $C_8$ to $C_{16}$ fatty alcohol sulfate, for example an ethoxylated $C_8$ to $C_{14}$ fatty alcohol sulfate. The weight proportion of the alkoxylated fatty alcohol sulfate in terms of the total weight of composition A and/or of composition B is for example from about 0.05 to about 30 wt. %, for example from about 0.1 to about 10 wt. %, such as from about 1.0 to about 5.0 wt. %.

The use of a polymeric thickening agent, in a further embodiment, is suitable for further improvement of the homogeneity and viscosity of the coloring agent for keratin fibers manufactured by the method contemplated herein. The thickening agent is for example added to composition A. From the extensive group of polymeric thickening agents, the use of polymeric thickening agents from the group of acrylic-acid or methacrylic-acid copolymers has proven particularly suitable for the manufacture of a coloring agent for keratin fibers having sufficient viscosity along with satisfactory homogeneity. A polymer that is particularly suitable is the copolymer known by the INCI name Acrylates Copolymer, made up of two or more monomers selected from acrylic acid, methacrylic acid, and esters thereof with $C_1$ to $C_6$ alkyl groups. In order to achieve advantageous viscosity and homogeneity values, the weight proportion of the polymeric thickener in terms of the total weight of composition A is for example from about 0.01 to about 50 wt. %, for example from about 0.1 to about 30 wt. %, such as from about 0.5 to about 20 wt. %.

Compositions A and B that are mixed with one another in the method can further contain, besides the obligatory constituents recited above, a plurality of hair-color-changing active substances. For example,
 two different oxidation dye precursors,
 two different substantive dyes,
 two oxidizing agents of different strength,
 an oxidizing agent and an oxidation dye precursor,
 an oxidizing agent and a substantive dye, or
 an oxidation dye precursor and a substantive dye can be mixed in the method to yield a coloring agent for keratin fibers.

In another embodiment, composition A contains an oxidizing agent and/or composition B contains a coloring agent from the group of oxidation dye precursors and substantive dyes.

In a further embodiment, composition A is flowable and is present in the form of a liquid, a gel, or a paste. Suitable liquid compositions A contain for example at least about 30 wt. %, for example at least about 40 wt. %, such as at least about 50 wt. % water. The weight proportion of water is for example in the range of from about 30 to about 98 wt. %, for example from about 40 to about 96 wt. %, such as from about 50 to about 94 wt. %, based in each case on the total weight of composition A.

In a variant of the method, composition A contains an oxidizing agent, for example from about 0.5 to about 50 wt. %, for example from about 1.0 to about 20 wt. %, for example from about 2.5 to about 16 wt. %, such as from about 5.0 to about 14 wt. % hydrogen peroxide (calculated as 100% $H_2O_2$), based in each case on the total weight of composition A.

Composition B can be present in flowable form, for example as a liquid, gel, or paste, but also as a solid, in particular as a powder or compressed powder. In terms of the duration of the method and in order to improve the method's results, in particular the mixing quality, however, flowable compositions B have proven advantageous as compared with solid ones.

The methods contemplated herein serve for simple and efficient manufacture of coloring agents for keratinic fibers. Corresponding agents therefore of course contain suitable coloring or decolorizing active substances. In this regard, composition B contains an oxidation dye precursor or a substantive dye.

In a first embodiment, composition B contains an oxidizing coloring agent (oxidation dye precursor).

"Oxidizing coloring agents" are to be understood as used herein as hair-color-changing agents that produce a permanent coloration of the fibers by the oxidation of oxidation dye precursors.

The methods contemplated herein are subject to no restrictions whatsoever with regard to the dye precursors usable in compositions B. Compositions B can contain, as dye precursors, oxidation dye precursors of the developer and/or coupler type, and precursors of bioanalogous dyes such as indole and indoline derivatives, as well as mixtures of representatives of these groups.

In the context of a first embodiment, compositions B contain an oxidation dye precursor of the developer and/or coupler type.

It may be suitable to use as a developer component a p-phenylenediamine derivative or one of its physiologically acceptable salts.

Particularly suitable p-phenylenediamines are selected from p-phenylenediamine, p-toluoylenediamine, 2-chloro-p-phenylenediamine, N,N-bis-(2-hydroxyethyl)-p-phenylenediamine and N-phenyl-p-phenylenediamine, 2-(2-hydroxyethyl)-p-phenylenediamine, N-(4-amino-3-methylphenyl)-N-[3-(1H-imidazol-1-yl)propyl]amine, as well as physiologically acceptable salts thereof.

It may furthermore be suitable to use as developer components compounds that contain at least two aromatic nuclei that are substituted with amino and/or hydroxyl groups.

Suitable binuclear developer components are, in particular, N,N'-bis-(2-hydroxyethyl)-N,N'-bis-(4'-aminophenyl)-1,3-diaminopropan-2-ol and bis-(2-hydroxy-5-aminophenyl)methane, and physiologically acceptable salts thereof.

It may furthermore be suitable to use as a developer component a p-aminophenol derivative or one of its physiologically acceptable salts.

Suitable p-aminophenols are, in particular, p-aminophenol, N-methyl-p-aminophenol, and 4-amino-3-methylphenol, as well as physiologically acceptable salts thereof.

The developer component can furthermore be selected from o-aminophenol and derivatives thereof such as, for example, 2-amino-5-methylphenol or physiologically acceptable salts thereof.

The developer component can moreover be selected from heterocyclic developer components such as, for example, the pyridine, pyrimidine, pyrazole, pyrazolopyrimidine derivatives and physiologically acceptable salts thereof.

Suitable pyrimidine derivatives are, in particular, 2,4,5,6-tetraminopyrimidine and 4-hydroxy-2,5,6-triaminopyrimidine, and physiologically acceptable salts thereof.

A suitable pyrazole derivative is 4,5-diamino-1-(2-hydroxyethyl)pyrazole and physiologically acceptable salts thereof.

In a further embodiment, compositions B contain a coupler component.

The coupler components generally used are m-phenylenediamine derivatives, naphthols, resorcinol and resorcinol derivatives, pyrazolones, and m-aminophenol derivatives. 1-Naphthol, 1,5- and 2,7-dihydroxynaphthalene, 1-acetoxy-2-methoxynaphthalene, resorcinol, 4-chlororesorcinol, and 2-amino-3-hydroxypyridine, and physiologically acceptable salts thereof, are suitable in particular as coupler substances.

Coupler components suitable for use are
(A) m-aminophenol and derivatives thereof such as, for example, 5-amino-2-methylphenol, 3-amino-2-chloro-6-methylphenol, 5-amino-4-chloro-2-methylphenol, 5-(2'-hydroxyethyl)amino-2-methylphenol, and 2,4-dichloro-3-aminophenol,
(B) o-aminophenol and derivatives thereof, for example 2-amino-5-ethylphenol,
(C) m-diaminobenzene and derivatives thereof such as, for example, 2,4-diaminophenoxyethanol, 1,3-bis-(2',4'-diaminophenoxy)propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}amino)ethanol,
(D) o-diaminobenzene and derivatives thereof,
(E) di- resp. trihydroxybenzene derivatives such as, for example, 2-methylresorcinol and 1,2,4-trihydroxybenzene,
(F) pyridine derivatives such as, for example, 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
(G) naphthalene derivatives such as, for example, 1-naphthol and 2-methyl-1-naphthol,
(H) morpholine derivatives such as, for example, 6-hydroxybenzomorpholine,
(I) quinoxaline derivatives,
(J) pyrazole derivatives such as, for example, 1-phenyl-3-methylpyrazol-5-one,
(K) indole derivatives such as, for example, 6-hydroxyindole,
(L) pyrimidine derivatives, or
(M) methylenedioxybenzene derivatives such as, for example, 1-(2'-hydroxyethyl)amino-3,4-methylenedioxybenzene,
as well as physiologically acceptable salts thereof.

Coupler components particularly suitable are 1-naphthol, 1,5- and 2,7-dihydroxynaphthalene, 5-amino-2-methylphenol, 2-amino-3-hydroxypyridine, resorcinol, 4-chlororesorcinol, 2-methylresorcinol, and 2,6-dihydroxy-3,4-dimethylpyridine, and physiologically acceptable salts thereof.

In an embodiment, compositions B used as contemplated herein contain both the developer components and the coupler components in a quantity from about 0.005 to about 20 wt. %, for example from about 0.1 to about 5 wt. %, based in each case on the total weight of composition B. Developer components and coupler components are, in this context, generally used in approximately molar quantities with respect to one another. Although molar utilization has proven useful, a certain excess of individual oxidation dye precursors is not disadvantageous, so that developer components and coupler components can be contained at a molar ratio from 1:0.5 to 1:3, in particular 1:1 to 1:2.

In a further embodiment, compositions B contain as an oxidation dye precursor a precursor of a bioanalogous dye. Those indoles and indolines that comprise at least one hydroxy or amino group, for example as a substituent on the six-membered ring, are suitable for use as precursors of bioanalogous dyes.

Particularly suitable derivatives of indoline are 5,6-dihydroxyindoline and 2,3-dioxoindoline (isatine), and physiologically acceptable salts thereof. A particularly suitable derivative of indole is 5,6-dihydroxyindole and physiologically acceptable salts thereof.

In an embodiment, compositions B contain the indole derivatives or indoline derivatives in a quantity of from about 0.05 to about 10 wt. %, for example from about 0.2 to about 5 wt. %, based in each case on their total weight.

In addition to the oxidation dye precursors or alternatively to those coloring agents, compositions B can also contain substantive dyes. In a further embodiment, compositions B contain a substantive dye. Substantive dyes can be subdivided into anionic, cationic, and nonionic substantive dyes. The substantive dyes are for example selected from the nitrophenylenediamines, nitroaminophenols, azo dyes, anthraquinones, or indophenols, and physiologically acceptable salts thereof.

Suitable anionic substantive dyes are, in particular, 2,4-dinitro-1-naphthol-7-sulfonic acid disodium salt (C.I. 10,316; Acid Yellow 1; Food Yellow No. 1), 2-(indane-1,3-dion-2-yl)quinoline-x,x-sulfonic acid (mixture of mono- and disulfonic acid) (C.I. 47,005; D&C Yellow No. 10; Food Yellow No. 13; Acid Yellow 3, Yellow 10), 5-hydroxy-1-(4-sulfophenyl)-4-[(4-sulfophenyl)azo]pyrazole-3-carboxylic acid trisodium salt (C.I. 19,140; Food Yellow No. 4; Acid Yellow 23), 3-[(4-phenylamino)phenyl]azobenzenesulfonic acid sodium salt (C.I. 13,065; Ki406; Acid Yellow 36), 4-[(2-hydroxynaphth-1-yl)azo]-benzenesulfonic acid sodium salt (C.I. 15,510; Acid Orange 7), 6-hydroxy-5-[(4-sulfonaphth-1-yl)azo]-2,4-naphthalenedisulfonic acid trisodium salt (C.I. 16,255; Ponceau 4R; Acid Red 18), 8-amino-1-hydroxy-2-

(phenylazo)-3,6-naphthalenedisulfonic acid disodium salt (C.I. 17,200; Acid Red 33), N-[6-(diethylamino)-9-(2,4-disulfophenyl)-3H-xanthen-3-ylidene]-N-ethylethanammonium hydroxide, internal salt, sodium salt (C.I. 45,100; Acid Red 52), 2',4',5',7'-tetrabromo-4,5,6,7-tetrachloro-3',6'-dihydroxyspiro[isobenzofuran-1(3H), 9191-1]xanthen-3-one disodium salt (C.I. 45,410; Acid Red 92), 3-hydroxy-4-[(4-methyl-2-sulfophenyl)azo]-2-naphthalenecarboxylic acid calcium salt (C.I. 15, 850:1; Pigment Red 57:1), 1,4-bis[(2-sulfo-4-methylphenyl)amino]-9,10-anthraquinone disodium salt (C.I. 61,570; Acid Green 25), bis[4-(dimethylamino)phenyl]-(3,7-disulfo-2-hydroxynaphth-1-yl)carbenium internal salt, sodium salt (C.I. 44,090; Food Green No. 4; Acid Green 50), N-[4-[(2,4-disulfophenyl)[4-[ethyl(phenylmethyl)amino)phenyl]methylene]-2,5-cyclohexadiene-1-ylidene]-N-ethylbenzenemethanaminium hydroxide, internal salt, sodium salt (C.I. 42,080; Acid Blue 7), (2-sulfophenyl)di[4-(ethyl((4-sulfophenyl)methyl)amino)phenyl]-carbenium disodium salt betaine (C.I. 42,090; Acid Blue 9; FD&C Blue No. 1), 1-amino-4-(cyclohexylamino)-9,10-anthraquinone-2-sulfonic acid sodium salt (C.I. 62,045; Acid Blue 62), 1-hydroxy-4-[(4-methyl-2-sulfophenyl)amino]-9,10-anthraquinone sodium salt (C.I. 60,730; D&C Violet No. 2; Acid Violet 43), 5-amino-4-hydroxy-6-[(4-nitrophenyl)azo]-3-(phenylazo)-2,7-naphthalenedisulfonic acid disodium salt (C.I. 20,470; Acid Black 1), 3-hydroxy-4-[(2-hydroxynaphth-1-yl)azo]-7-nitro-1-naphthalenesulfonic acid chromium complex (3:2) (C.I. 15,711; Acid Black 52), and 3',3'',4,5,5',5'',6,7-octabromophenolsulfonphthalein (tetrabromophenol blue).

Suitable anionic substantive dyes are the compounds known by the international designations resp. trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Suitable as cationic substantive dyes are, in particular, di[4-(diethylamino)phenyl][4-(ethylamino)naphthyl]carbenium chloride (C.I. 42,595; Basic Blue 7), di[4-(dimethylamino)phenyl][4-(phenylamino)naphthyl]carbenium chloride (C.I. 44,045; Basic Blue 26), 8-amino-2-bromo-5-hydroxy-4-imino-6-[(3-(trimethylammonio)phenyl)amino]-1(4H)-naphthalenone chloride (C.I. 56,059; Basic Blue No. 99), tri(4-amino-3-methylphenyl)carbenium chloride (C.I. 42,520; Basic Violet 2), di(4-aminophenyl)(4-amino-3-methylphenyl)carbenium chloride (C.I. 42,510 Basic Violet 14), 1-[(4-aminophenyl)azo]-7-(trimethylammonio)-2-naphthol chloride (C.I. 12,250; Basic Brown 16), 1-[(4-amino-2-nitrophenyl)azo]-7-(trimethylammonio)-2-naphthol chloride, 1-[(4-amino-3-nitrophenyl)azo]-7-(trimethylammonio)-2-naphthol chloride (C.I. 12,251; Basic Brown 17), 3-[(4-amino-2,5-dimethoxyphenyl)azo]-N,N,N-trimethylbenzenaminium chloride (C.I. 12,605, Basic Orange 69), 2-[((4-dimethylamino)phenyl)azo]-1,3-dimethyl-1H-imidazolium chloride (Basic Red 51), 2-hydroxy-1-[(2-methoxyphenyl)azo]-7-(trimethylammonio)naphthalene chloride (C.I. 12,245; Basic Red 76), 2-[4-aminophenyl)azo]-1,3-dimethyl-1H-imidazolium chloride (Basic Orange 31), 3-methyl-1-phenyl-4-[(3-(trimethylammonio)phenyl)azo]pyrazol-5-one chloride (C.I. 12,719; Basic Yellow 57), 1-methyl-4-((methylphenylhydrazono)methyl)pyridinium methylsulfate (Basic Yellow 87), 1-(2-morpholiniumpropylamino)-4-hydroxy-9,10-anthraquinone methylsulfate, 4-formyl-1-methylquinolonium-p-toluenesulfonate, and substantive dyes which contain a heterocycle that comprises at least one quaternary nitrogen atom.

Nonionic nitro and quinone dyes, and neutral azo dyes, are particularly suitable as nonionic substantive dyes.

Suitable blue nitro dyes are, in particular, 1,4-bis[(2-hydroxyethyl)amino]-2-nitrobenzene (HC Violet BS), 1-(2-hydroxyethyl)amino-2-nitro-4-[di(2-hydroxyethyl)amino]benzene (HC Blue 2), 4-[di(2-hydroxyethypamino]-1-[(2-methoxyethyl)amino]-2-nitrobenzene (HC Blue 11), 4-[ethyl-(2-hydroxyethyl)amino]-1-[(2-hydroxyethyl)amino]-2-nitrobenzene hydrochloride (HC Blue 12), 1-(2-hydroxyethyl)amino-2-nitro-4-N-ethyl-N-(2-hydroxyethyl)aminobenzene (HC Blue 15), 1-amino-3-methyl-4-[(2-hydroxyethyl)amino]-6-nitrobenzene (HC Violet 1), and 1-(3-hydroxypropylamino)-4-[di(2-hydroxyethyl)amino]-2-nitrobenzene (HC Violet 2).

Suitable red nitro dyes are, in particular, 1-amino-4-[(2-hydroxyethyl)amino]-2-nitrobenzene (HC Red 7), 2-amino-4,6-dinitrophenol (picramic acid) and salts thereof, 1,4-diamino-2-nitrobenzene (C.I. 76,070), 4-amino-2-nitrodiphenylamine (HC Red 1), 1-amino-4-[di(2-hydroxyethyl)amino]-2-nitrobenzene hydrochloride (HC Red 13), 1-amino-4-[(2-hydroxyethyl)amino]-5-chloro-2-nitrobenzene, 4-amino-1-[(2-hydroxyethyl)amino]-2-nitrobenzene (HC Red 3), 4-[(2-hydroxyethyl)amino-3-nitrotoluene, 4-amino-3-nitrophenol, 4-[(2-hydroxyethyl)amino]-3-nitrophenol, 4-[(2-nitrophenyl)amino]phenol (HC Orange 1), 1-[(2-aminoethyl)amino]-4-(2-hydroxyethoxy)-2-nitrobenzene (HC Orange 2), 1-amino-5-chloro-4-[(2,3-dihydroxypropyl)amino]-2-nitrobenzene (HC Red 10), 5-chloro-1,4-[di(2,3-dihydroxypropyl)amino]-2-nitrobenzene (HC Red 11), 2-[(2-hydroxyethyl)amino-4,6-dinitrophenol and salts thereof, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol (HC Red BN), 1,2,3,4-tetrahydro-6-nitroquinoxaline, and 6-hydroxy-5-((2-methoxy-5-methyl-4-sulfophenyl)azo)-2-naphthalenesulfonic acid (Curry Red).

Suitable yellow nitro dyes are, in particular, 1,2-diamino-4-nitrobenzene (C.I. 76,020), 1-[(2-hydroxyethyl)amino]-2-nitrobenzene (HC Yellow 2), 1-(2-hydroxyethoxy)-2-[(2-hydroxyethyl)amino]-5-nitrobenzene (HC Yellow 4), 1-amino-2-[(2-hydroxyethyl)amino]-5-nitrobenzene (HC Yellow 5), 4-[(2,3-dihydroxypropyl)amino]-3-nitro-1-trifluoromethylbenzene (HC Yellow 6), 2-[(2-hydroxyethyl)amino]-1-methoxy-5-nitrobenzene, 2-amino-4-nitrophenol, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene hydrochloride (HC Yellow 9), 1-chloro-2,4-bis[(2-hydroxyethyl)amino]-5-nitrobenzene (HC Yellow 10), 2-[(2-hydroxyethyl)amino]-5-nitrophenol (HC Yellow 11), 1-[(2'-ureidoethyl)amino]-4-nitrobenzene, 1-amino-4-[(2-aminoethyl)amino]-5-methyl-2-nitrobenzene, 4-[(2-hydroxyethyl)amino]-3-nitro-1-methyl benzene, 1-chloro-4-[(2-hydroxyethyl)amino]-3-nitrobenzene (HC Yellow 12), and 4-[(2-hydroxyethyl)amino]-3-nitro-1-trifluoromethylbenzene (HC Yellow 13).

Suitable quinone dyes are, in particular, 1-[(2-hydroxyethyl)amino]-4-methylamino-9,10-anthraquinone (C.I. 61,505, Disperse Blue 3), mixtures of 1,4-bis[(2-hydroxyethyl)amino]anthra-9,10-quinone with 1-[(2-hydroxyethyl)amino]-4-[(3-hydroxypropyl)amino]anthra-9,10-quinone and 1,4-bis[(3-hydroxypropyl)amino]anthra-9,10-quinone (Disperse Blue 377), 1,4-diamino-9,10-anthraquinone (C.I. 61,100, Disperse Violet 1), 1-amino-4-(methylamino)-9,10-anthraquinone (C.I. 61,105, Disperse Violet 4, Solvent Violet No. 12), 2-hydroxy-1,4-naphthoquinone (Lawsone, C.I.

75,480, Natural Orange 6), and 1,4-bis[(2,3-dihydroxypropyl)amino]-9,10-anthracenedione (HC Blue 14).

Suitable neutral azo dyes are, in particular, 1-[di(2-hydroxyethyl)amino]-3-methyl-4-[(4-nitrophenyl)azo]benzene (C.I. 11,210, Disperse Red 17), 1-[di(2-hydroxyethyl)amino]-4-[(4-nitrophenyl)azo]benzene (Disperse Black 9), 4-[(4-aminophenyl)azo]-1-[di(2-hydroxyethyl)amino]-3-methylbenzene (HC Yellow 7), 2,6-diamino-3-[(pyridin-3-yl)azo]pyridine, and 4-[(4-nitrophenyl)azo]aniline (C.I. 11,005; Disperse Orange 3).

Compositions B contain the substantive dyes, for example, in a quantity from about 0.01 to about 20 wt. %, based on the total weight of composition B.

The agents can furthermore also contain naturally occurring dyes, for example indigo (*Indigoferia tinctoria*), red henna (*Lawsonia inermis*), neutral henna, or black henna. Further suitable natural dyes are contained, for example, in chamomile blossoms, sandalwood, black tea, buckthorn bark, salvia, logwood, madder root, catechu, Spanish cedar, and alkanna root.

In a third embodiment, a hair-bleaching agent, for example, a hair-bleaching powder, is used as composition B. To generate the hair-bleaching effect, these hair-bleaching agents may contain so-called "boosters." These are as a rule solid peroxo compounds that do not represent addition products of hydrogen peroxide with other components. The selection of these peroxo compounds is not subject, in principle, to any limitations; usual peroxo compounds known to one skilled in the art are, for example, ammonium peroxodisulfate, potassium peroxodisulfate, sodium peroxodisulfate, ammonium persulfate, potassium persulfate, sodium persulfate, potassium peroxodiphosphate, percarbonates such as magnesium percarbonate, and peroxides such as barium peroxide. Among these peroxo compounds, which can also be used in combination, the inorganic compounds are particularly suitable. The peroxodisulfates, in particular ammonium peroxodisulfate, are particularly suitable.

According to an embodiment, the peroxo compounds are contained in the hair-bleaching agents used as composition B in quantities from about 2 to about 50 wt. %, in particular in quantities from about 10 to about 35 wt. %. In another embodiment, composition B contains an oxidizing agent, for example from about 5.0 to about 50 wt. %, for example from about 10 to about 45 wt. %, for example from about 15 to about 40 wt. %, such as from about 20 to about 35 wt. % persulfate, based in each case on the total weight of composition B.

In another embodiment, as a further component, the hair-bleaching agents contain an alkalizing agent that serves to establish the alkaline pH of the utilization mixture. The usual alkalizing agents likewise known to one skilled in the art for hair-bleaching agents can be used, for example hydroxides, carbonates, hydrogen carbonates, hydroxycarbonates, silicates, in particular metasilicates of ammonium, alkali metals, and alkaline earth metals, as well as alkali phosphates. In an embodiment, the hair-bleaching agents contain at least two different alkalizing agents. Mixtures of, for example, a hydroxycarbonate and a metasilicate can be suitable in this context.

The weight proportion of the alkalizing agent in terms of the total weight of the hair-bleaching agent used as composition B is for example from about 5 to about 50 wt. %, for example from about 10 to about 45 wt. %, such as from about 12 to about 40 wt. %.

If a hair-bleaching agent is used as composition B, the agent is present for example in powder form, a component for dedusting the finely powdered formulation usually additionally being added. Such dedusting agents are usually oils, liquid waxes, ether derivatives, but also solvents that are liquid at about 25° C., selected from the group of hydrocarbons, alcohols, esters, and ketones, for example 3-methoxybutanol, benzyl alcohol, 1,2-propanediol, hexanol, cyclohexanone, propylene carbonate, and ethyl diglycol.

Composition B can contain a thickening agent to adjust the viscosity; solid compositions B in particular, in particular solid, bleaching-agent-containing compositions B, containing for example from about 0.5 to about 20 wt. %, for example from about 1.0 to about 15 wt. %, such as from about 1.5 to about 10 wt. % xanthan and/or carboxy cellulose.

Some of the combinations of composition A and composition B used in the method contemplated herein may be gathered from the following tables. The data are provided for illustration purposes only and are not meant to limit the various embodiments in any way:

| | 1 | 2 | 3 | 4 |
|---|---|---|---|---|
| Composition A: indications in wt % based on composition A | | | | |
| Oxidizing agent | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Oxidation dye precursor | 0.005 to 20 | 0.01 to 10 | 0.1 to 5.0 | 0.1 to 3.0 |
| Fatty alcohol | 0.1 to 10 | 0.15 to 8.0 | 0.15 to 8.0 | 0.2 to 6.0 |
| Alkoxylated fatty alcohol | 0.1 to 40 | 1.0 to 30 | 2.0 to 20 | 2.0 to 20 |
| Fatty acid | 1.0 to 20 | 2.0 to 18 | 2.0 to 18 | 5.0 to 15 |
| Misc. | to 100 | to 100 | to 100 | to 100 |

| | 5 | 6 | 7 | 8 |
|---|---|---|---|---|
| Composition A: indications in wt % based on composition A | | | | |
| Oxidizing agent | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Substantive dye | 0.01 to 20 | 0.1 to 15 | 0.2 to 10 | 0.5 to 5.0 |
| Fatty alcohol | 0.1 to 10 | 0.15 to 8.0 | 0.15 to 8.0 | 0.2 to 6.0 |
| Alkoxylated fatty alcohol | 0.1 to 40 | 1.0 to 30 | 2.0 to 20 | 2.0 to 20 |
| Fatty acid | 1.0 to 20 | 2.0 to 18 | 2.0 to 18 | 5.0 to 15 |
| Misc. | to 100 | to 100 | to 100 | to 100 |

| | 9 | 10 | 11 | 12 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Oxidation dye precursor | 0.005 to 20 | 0.01 to 10 | 0.1 to 5.0 | 0.1 to 3.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Misc. | to 100 | to 100 | to 100 | to 100 |

|  | 13 | 14 | 15 | 16 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Substantive dye | 0.01 to 20 | 0.1 to 15 | 0.2 to 10 | 0.5 to 5.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Misc. | to 100 | to 100 | to 100 | to 100 |

|  | 17 | 18 | 19 | 20 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Oxidation dye precursor | 0.005 to 20 | 0.01 to 10 | 0.1 to 5.0 | 0.1 to 3.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Oil component (mp < 25° C.) * | 0.1 to 50 | 1.0 to 40 | 5.0 to 20 | 5.0 to 30 |
| Misc. | to 100 | to 100 | to 100 | to 100 |

* preferably paraffin

|  | 21 | 22 | 23 | 24 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| Misc. | to 100 | to 100 | to 100 | to 100 |
| Composition B: indications in wt % based on composition B | | | | |
| Substantive dye | 0.01 to 20 | 0.1 to 15 | 0.2 to 10 | 0.5 to 5.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Oil component (mp < 25° C.) * | 0.1 to 50 | 1.0 to 40 | 5.0 to 20 | 5.0 to 30 |
| Misc. | to 100 | to 100 | to 100 | to 100 |

* preferably paraffin

|  | 25 | 26 | 27 | 28 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| (Meth)acrylic acid copolymer thickener | 0.01 to 50 | 0.1 to 30 | 0.5 to 20 | 0.5 to 10 |
| Misc. | to 100 | to 100 | to 100 | to 100 |
| Composition B: indications in wt % based on composition B | | | | |
| Oxidation dye precursor | 0.005 to 20 | 0.01 to 10 | 0.1 to 5.0 | 0.1 to 3.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Misc. | to 100 | to 100 | to 100 | to 100 |

|  | 29 | 30 | 31 | 32 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| (Meth)acrylic acid copolymer thickener | 0.01 to 50 | 0.1 to 30 | 0.5 to 20 | 0.5 to 10 |
| Misc. | to 100 | to 100 | to 100 | to 100 |
| Composition B: indications in wt % based on composition B | | | | |
| Substantive dye | 0.01 to 20 | 0.1 to 15 | 0.2 to 10 | 0.5 to 5.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Misc. | to 100 | to 100 | to 100 | to 100 |

|  | 33 | 34 | 35 | 36 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| (Meth)acrylic acid copolymer thickener | 0.01 to 50 | 0.1 to 30 | 0.5 to 20 | 0.5 to 10 |
| Misc. | to 100 | to 100 | to 100 | to 100 |
| Composition B: indications in wt % based on composition B | | | | |
| Oxidation dye precursor | 0.005 to 20 | 0.01 to 10 | 0.1 to 5.0 | 0.1 to 3.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Oil component (mp < 25° C.) * | 0.1 to 50 | 1.0 to 40 | 5.0 to 20 | 5.0 to 30 |
| Misc. | to 100 | to 100 | to 100 | to 100 |

* preferably paraffin

|  | 37 | 38 | 39 | 40 |
|---|---|---|---|---|
| Composition A: indications in wt % based on composition A | | | | |
| Hydrogen peroxide | 0.5 to 50 | 1.0 to 20 | 2.5 to 16 | 5.0 to 14 |
| (Meth)acrylic acid copolymer thickener | 0.01 to 50 | 0.1 to 30 | 0.5 to 20 | 0.5 to 10 |
| Misc. | to 100 | to 100 | to 100 | to 100 |
| Composition B: indications in wt % based on composition B | | | | |
| Substantive dye | 0.01 to 20 | 0.1 to 15 | 0.2 to 10 | 0.5 to 5.0 |
| $C_{12}$ to $C_{16}$ fatty alcohol | 0.1 to 10 | 0.15 to 8.0 | 0.15 to 8.0 | 0.2 to 6.0 |
| Alkoxylated $C_8$ to $C_{14}$ fatty alcohol | 0.1 to 40 | 1.0 to 30 | 2.0 to 20 | 2.0 to 20 |
| $C_{12}$ to $C_{22}$ fatty acid | 1.0 to 20 | 2.0 to 18 | 2.0 to 18 | 5.0 to 15 |
| Oil component (mp < 25° C.) * | 0.1 to 50 | 1.0 to 40 | 5.0 to 20 | 5.0 to 30 |
| Misc. | to 100 | to 100 | to 100 | to 100 |

* preferably paraffin

The coloring agents manufactured as contemplated herein with compositions A and B used for manufacture can contain further active substances, adjuvants, and additives such as, for example:

nonionic polymers such as, for example, vinylpyrrolidone/ vinyl acrylate copolymers, polyvinylpyrrolidone, vinylpyrrolidone/vinyl acetate copolymers, and polysiloxanes, cationic polymers such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidone copolymers quaternized with diethyl sulfate, vinylpyrrolidone/imidazolinium methochloride copolymers, and quaternized polyvinyl alcohol, zwitterionic and amphoteric polymers such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert-butylacrylamide terpolymers, thickening agents such as agar-agar, guar gum, alginates, xanthan gum, gum arabic, karaya gum, locust bean flour, linseed gums, dextrans, cellulose derivatives, e.g. methyl cellulose, hydroxyalkyl cellulose, and carboxymethyl cellulose, starch fractions and derivatives such as amylose, amylopectin, and dextrins, clays such as e.g. bentonite, or entirely synthetic hydrocolloids such as, for example, polyvinyl alcohol, structuring agents such as maleic acid and lactic acid, hair-conditioning compounds such as phospholipids, for example soy lecithins, egg lecithin, and kephalins, protein hydrolysates, in particular hydrolysates of elastin, collagen, keratin, milk protein, soy protein, and wheat protein, condensation products thereof with fatty acids, and quaternized protein hydrolysates, perfume oils, dimethylisosorbide, and cyclodextrins, solvents and solubilizers such as ethanol, isopropanol, ethylene glycol, propylene glycol, and diethylene glycol, fiber-structure-improving active substances, in particular mono-, di- and oligosaccharides such as, for example, glucose, galactose, fructose, fruit sugars, and lactose, quaternized amines such as methyl-1-alkylamidoethyl-2-alkylimidazolinium methosulfate, defoamers such as silicones, dyes for coloring the agent, anti-dandruff active substances such as piroctone olamide, zinc omadine, and climbazol, light-protection agents, in particular derivatized benzophenones, cinnamic acid derivatives, and triazines, substances for adjusting pH, such as e.g. usual acids, in particular edible acids, and bases, active substances such as allantoin, pyrrolidonecarboxylic acids and salts thereof, as well as bisabolol;

vitamins, provitamins, and vitamin precursors, in particular those of groups A, $B_3$, $B_5$, $B_6$, C, E, F, and H, plant extracts such as the extracts from green tea, oak bark, nettle, hamamelis, hops, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root, cholesterol, consistency agents such as sugar esters, polyol esters, or polyolalkyl ethers, fats and waxes such as spermaceti, beeswax, Montan wax, and paraffins, fatty acid alkanolamides, complexing agents such as EDTA, NTA, β-alaninediacetic acid, and phosphonic acids, swelling and penetration substances such as glycerol, propylene glycol monoethyl ether, carbonates, hydrogen carbonates, guanidines, ureas, and primary, secondary, and tertiary phosphates, opacifiers such as latex, styrene/PVP and styrene/acrylamide copolymers, luster agents such as ethylene glycol mono- and distearate as well as PEG-3 distearate, preservatives, stabilizing agents for hydrogen peroxide and other oxidizing agents, propellants such as propane/butane mixtures, $N_2O$, dimethyl ether, $CO_2$, and air, and antioxidants.

As stated previously, the methods as contemplated herein serve in particular for manufacturing coloring agents for human hair. Suitable methods are therefore characterized in that the coloring agent for keratin fibers is applied, after exiting from container B, onto keratin fibers, by preference human hair. Application of the coloring agent occurs for example immediately, i.e., within a period of less than about 30 minutes, for example less than 15 minutes, for example less than about 10 minutes, such as less than about 5 minutes.

A method for manufacturing a coloring agent for keratin fibers from a flowable composition A and a composition B, according to an embodiment, in which method the first composition A is directed from a container A
by a filler apparatus
through an inlet opening
into a container B containing the composition B, and the coloring agent for keratin fibers exits from container B as a mixture of compositions A and B, wherein
a) composition A contains
about 0.5 to about 50 wt. % of an oxidizing agent,
b) composition B contains
a fatty alcohol,
an alkoxylated fatty alcohol, and
a fatty acid wherein composition A is introduced into container B at a pressure above about 1.1 bar, for example above about 2.0 bar, for example above about 5.0 bar, such as in the range of from about 10 to about 20 bar, and container B forms, as a result of the introduction of composition A, an exit opening from which the coloring agent for keratin fibers exits from container B as a mixture of compositions A and B, is provided.

Also provided according to an embodiment is a container encompassing a container wall closing off the container on the outside,
a weakening line integrated into the container wall, and
a composition, present in the container, including
a) a fatty alcohol,
b) an alkoxylated fatty alcohol, and
c) a fatty acid.

According to another embodiment, a container is provided encompassing
a container wall closing off the container on the outside,
a weakening line integrated into the container wall,
a static mixer integrated into the container, and
a composition, present in the container, encompassing
a) a fatty alcohol,
b) an alkoxylated fatty alcohol, and
c) a fatty acid.

According to a further embodiment, a container encompasses
a container wall closing off the container on the outside,
a spike that is suitable for penetrating the container wall upon exertion of a force on the spike and/or on the container wall, and
a composition, present in the container, containing
a) a fatty alcohol,
b) an alkoxylated fatty alcohol, and
c) a fatty acid.

Also provided according to an embodiment is a container encompassing
a container wall closing off the container on the outside,
a spike that is suitable for penetrating the container wall upon exertion of a force on the spike and/or on the container wall,
a static mixer integrated into the container, and
a composition, present in the container, containing
a) a fatty alcohol,
b) an alkoxylated fatty alcohol, and
c) a fatty acid.

The weight proportion of the oxidation dye precursors in terms of the total weight of the compositions present in the aforesaid containers is, according to an embodiment, from about 0.005 to about 20 wt. %.

The weight proportion of the substantive dyes in terms of the total weight of the compositions present in the aforesaid containers is, according to an embodiment, from about 0.01 to about 20 wt. %.

With regard to the chemical nature of the oxidation dye precursor and of the substantive dye, and of the other optional ingredients of the container, reference is made to the statements above in order to avoid repetition.

The volume of the aforesaid containers is, according to an embodiment, from about 5 to about 100 ml, for example from about 10 to about 80 ml, such as from about 20 to 60 ml.

Suitable containers have a cylindrical lateral surface, a planar upper side, and an underside of planar or conical configuration located opposite the upper side. Particularly suitable containers comprise a flange on which is fastened a sealing film closing off the container. A flange of this kind facilitates, for example, fastening of the container by an adhesive, latching, snap-on, or clamping mechanism in the apparatus used to carry out the method contemplated herein.

The aforesaid containers are produced, according to an embodiment, from chemically inert materials. The group of those materials includes, for example, aluminum, or plastics such as polypropylene.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. A method for manufacturing a coloring agent for keratin fibers, the method comprising the steps of:
directing a composition A from a container A by a filler apparatus through an inlet opening into a container B containing a composition B;
causing the coloring agent for keratin fibers to exit from the container B as a mixture of the composition A and the composition B,
wherein the composition B comprises:
a fatty alcohol,
an alkoxylated fatty alcohol, and
a fatty acid.

2. The method according to claim 1, wherein the composition A is introduced into the container B at a pressure above about 1.1 bar.

3. The method according to claim 2, wherein the composition A is introduced into the container B at the pressure above about 2.0 bar.

4. The method according to claim 3, wherein the composition A is introduced into the container B at the pressure above about 5.0 bar.

5. The method according to claim 4, wherein the composition A is introduced into the container B at the pressure in a range of from about 10 to about 20 bar.

6. The method according to claim 1, wherein the container B forms, as a result introduction of composition A and/or action of the filler apparatus, an exit opening from which the coloring agent for keratin fibers exits from the container B as the mixture of the composition A and the composition B.

7. The method according to claim 1, wherein the container B comprises an interior and having in its interior a static mixing element.

8. The method according to claim 1, wherein the composition B comprises the fatty alcohol chosen from $C_8$ to $C_{22}$ fatty alcohols and wherein a weight proportion of the fatty alcohol in terms of a total weight of the composition B is from about 0.1 to about 10 wt. %.

9. The method according to claim 8, wherein the composition B comprises the fatty alcohol chosen from $C_{10}$ to $C_{20}$ fatty alcohols.

10. The method according to claim 9, wherein the composition B comprises the fatty alcohol chosen from $C_{12}$ to $C_{18}$ fatty alcohols.

11. The method according to claim 8, wherein the weight proportion of the fatty alcohol in terms of the total weight of the composition B is from about 0.15 to about 8.0 wt. %.

12. The method according to claim 11, wherein the weight proportion of the fatty alcohol in terms of the total weight of the composition B is from about 0.2 to about 6.0 wt. %.

13. The method according to claim 1, wherein the composition B comprises the alkoxylated fatty alcohol chosen from ethoxylated fatty alcohols and wherein a weight proportion of the alkoxylated fatty alcohol in terms of a total weight of the composition B is from about 0.1 to about 40 wt. %.

14. The method according to claim 13, wherein the composition B comprises the alkoxylated fatty alcohol chosen from ethoxylated $C_8$ to $C_{16}$ fatty alcohols.

15. The method according to claim 13, wherein the weight proportion of the alkoxylated fatty alcohol in terms of the total weight of the composition B is from about 1.0 to about 30 wt. %.

16. The method according to claim 1, wherein the composition B contains the fatty acid chosen from $C_8$ to $C_{24}$ fatty acids and wherein a weight proportion of the fatty acid in terms of a total weight of the composition B is from about 1.0 to about 20 wt. %.

17. The method according to claim 1, wherein a weight ratio of the composition A and the composition B is in a range of from about 1:1 to about 20:1.

18. The method according to claim 17, wherein the weight ratio of the composition A and the composition B is in a range of from about 2:1 to about 10:1.

19. The method according to claim 1, wherein the coloring agent for keratin fibers has a viscosity greater than about 20,000 mPas (Brookfield viscosimeter, spindle 5, 4 rpm).

20. The method according to claim 1, wherein the coloring agent for keratin fibers is applied onto hair after exiting from the container B.

* * * * *